United States Patent
Kim et al.

(10) Patent No.: US 8,461,860 B2
(45) Date of Patent: Jun. 11, 2013

(54) BENDING TEST APPARATUS FOR FLEXIBLE DEVICES

(75) Inventors: Yong Hae Kim, Daejeon (KR); Gi Heon Kim, Daejeon (KR); Seung Youl Kang, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 355 days.

(21) Appl. No.: 12/856,127

(22) Filed: Aug. 13, 2010

(65) Prior Publication Data

US 2011/0248739 A1      Oct. 13, 2011

(30) Foreign Application Priority Data

Apr. 13, 2010   (KR) .................. 10-2010-0033801

(51) Int. Cl.
   *G01R 31/02*   (2006.01)
   *G01N 3/20*    (2006.01)

(52) U.S. Cl.
   USPC ........................................ 324/762.01; 73/849

(58) Field of Classification Search
   None
   See application file for complete search history.

(56) References Cited

U.S. PATENT DOCUMENTS

| | | | |
|---|---|---|---|
| 6,776,050 B2 * | 8/2004 | Auch et al. ...................... | 73/849 |
| 2001/0024124 A1 * | 9/2001 | Kawakita et al. ............. | 324/503 |
| 2003/0061885 A1 | 4/2003 | Auch et al. | |
| 2007/0256503 A1 * | 11/2007 | Wong et al. ..................... | 73/812 |
| 2012/0285257 A1 * | 11/2012 | Kim ............................... | 73/849 |

FOREIGN PATENT DOCUMENTS

| | | |
|---|---|---|
| KR | 20-0281592 | 6/2002 |
| KR | 10-2010-0016826 A | 2/2010 |

* cited by examiner

*Primary Examiner* — Jermele M Hollington
(74) *Attorney, Agent, or Firm* — Rabin & Berdo, P.C.

(57) ABSTRACT

Provided is a bending test apparatus of a flexible device. The bending test apparatus includes: first and second electrode parts disposed in a horizontal direction and loading a flexible device horizontally, wherein the first electrode part is movable in the horizontal direction and the second electrode part is fixed so that the first electrode part horizontally moves toward the second electrode part to apply mechanical stress of the horizontal direction to the flexible device.

20 Claims, 10 Drawing Sheets

BENDING TEST APPARATUS FOR FLEXIBLE DEVICES

CROSS-REFERENCE TO RELATED APPLICATIONS

This U.S. non-provisional patent application claims priority under 35 U.S.C. §119 of Korean Patent Application No. 10-2010-0033801, filed on Apr. 13, 2010, the entire contents of which are hereby incorporated by reference.

BACKGROUND OF THE INVENTION

The present invention disclosed herein relates to a test apparatus for a semiconductor device, and more particularly, to a bending test apparatus for a flexible device, which achieves the reliability of an electrical and mechanical stress test.

Since a display device manufactured on a glass substrate does not have a bending property, reliability research related to electrical stress is mainly performed. However, since a flexible display device manufactured on a flexible substrate has a bending property, it undergoes electrical and mechanical stresses. Therefore, measuring reliability related to mechanical stress of a thin film deposited on a plastic substrate and a flexible device is required.

SUMMARY OF THE INVENTION

The present invention provides a bending test apparatus for a flexible device, which achieves the reliability of an electrical and mechanical stress test.

Embodiments of the present invention provide bending test apparatuses of a flexible device including: first and second electrode parts disposed in a horizontal direction and loading a flexible device horizontally, wherein the first electrode part is movable in the horizontal direction and the second electrode part is fixed so that the first electrode part horizontally moves toward the second electrode part to apply mechanical stress of the horizontal direction to the flexible device.

In some embodiments, at least one of the first and second electrode parts may be rotatable based on a rotation axis vertical to the horizontal direction.

In other embodiments, the apparatuses may further include a supporter disposed between the first and second electrode parts and preventing the flexible device to which the mechanical stress of the horizontal direction is applied from being bent in a gravity direction.

In still other embodiments, the apparatuses may further include an electric device providing electrical signals to the first and second electrode parts to apply electrical stress to the flexible device.

In even other embodiments, bending test apparatuses of a flexible device include: a motor generating a rotating power; a cam connected to the motor and eccentrically rotating by receiving the rotating power; a carrier linearly moving in a horizontal direction by the eccentric rotation of the cam; a rotatable first electrode part fixed at the carrier and moving in the horizontal direction depending on the linear movement of the carrier; and a rotatable second electrode part fixed and spaced apart from the first electrode part in the horizontal direction.

In yet other embodiments, the motor may be movable in the horizontal direction.

In further embodiments, the cam and the carrier may be disposed in the horizontal direction.

In still further embodiments, the horizontal direction may have opposite first and second horizontal directions; the first electrode part may move toward the second electrode part depending on movement to the second horizontal direction of the carrier; and a distance between the first and second electrode parts may be reduced by the movement of the first electrode part to apply mechanical stress of the horizontal direction to the flexible device.

In even further embodiments, the apparatuses may further include a spring combined to the carrier and restoring the carrier to the first horizontal direction.

In yet further embodiments, the apparatuses may further include a stopper disposed between the carrier and the cam and preventing excessive movement of the carrier to the first horizontal direction that exceeds a restoring position of the carrier.

In yet further embodiments, the stopper may be movable in the horizontal direction.

In yet further embodiments, at least one of the first and second electrode parts may include: a roller including a groove into which the flexible device is inserted; at least one electrode disposed in the roller and electrically contacting the flexible device inserted into the groove; and a electrode body installed and allowing the roller to be rotatable, wherein the roller rotates when the flexible device is bent to apply uniform mechanical stress to the flexible device.

In yet further embodiments, the apparatuses may further include a probe of a terminal connection structure applying electrical stress to the flexible device by applying an electrical signal to the at least one electrode.

In yet further embodiments, the apparatuses may further include a supporter disposed between the first and second electrode parts, having a height identical to or higher than a radius of the roller and preventing the flexible device from being bent in a gravity direction.

In yet further embodiments, the apparatuses may further include at least one of a first ruler estimating a position of the motor and a second ruler estimating a distance between the first and second electrode parts.

In yet further embodiments, a rotation axis of the cam may be offset with respect to a rotation axis of the motor.

In yet further embodiments, the apparatuses may further include a frame providing a place into which the first and second electrode parts and the carrier are installed, the frame including a first moving groove that guides the carrier in the horizontal direction.

In yet further embodiments, the frame may further include a second moving groove changing a position of the motor and a third moving groove changing a position of the stopper.

In other embodiments of the present invention, bending test apparatuses of a flexible device include: a device converting a rotating motion into a linear reciprocating motion; a first electrode part combined with the device and providing a linear reciprocating motion together in company with the device; and a second electrode part disposed being horizontally spaced apart from the first electrode part and horizontally loading the flexible device between the first electrode part and the second electrode part, wherein the first electrode part linearly moves toward the second electrode part to bend the flexible device vertically.

In some embodiments, the device may include: a motor generating the rotating motion; a carrier combined with the first electrode part and providing the linear reciprocating motion by receiving the rotating motion; and a cam combined with the motor, eccentrically rotating by the rotating motion, and linearly moving the carrier toward the second electrode part, wherein the cam converts the rotating motion of the motor into the linter reciprocating motion of the carrier.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Hereinafter, a bending test apparatus of a flexible device will be described with reference to the accompanying drawings.

Preferred embodiments of the present invention will be described below in more detail with reference to the accompanying drawings. The present invention may, however, be embodied in different forms and should not be constructed as limited to the embodiments set forth herein. Rather, these embodiments are provided so that this disclosure will be thorough and complete, and will fully convey the scope of the present invention to those skilled in the art. Like reference numerals refer to like elements.

Figure 1A:
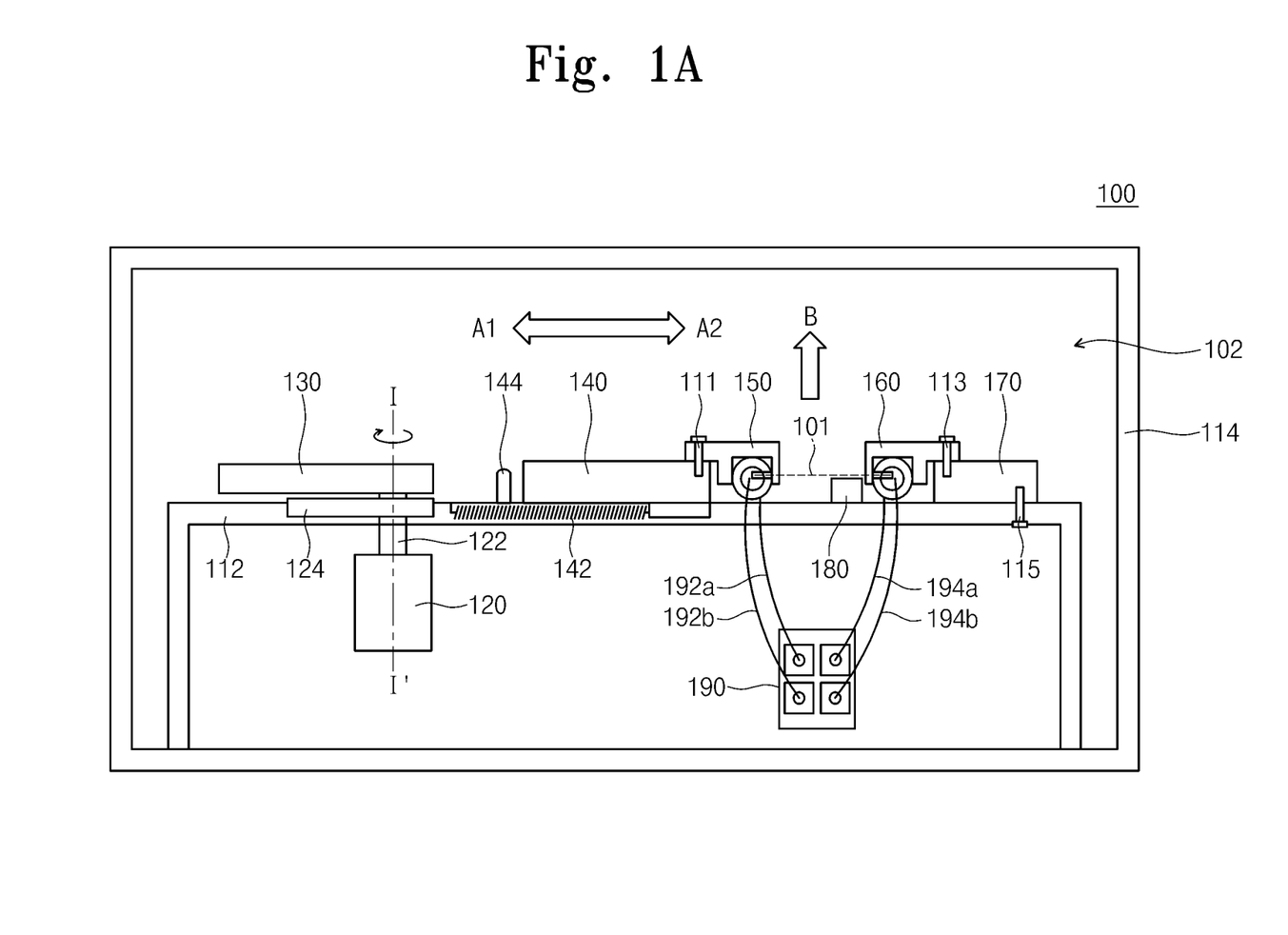
FIG. 1A is a sectional view illustrating a bending test apparatus for a flexible device according to an embodiment of the present invention.
Figure 1B:
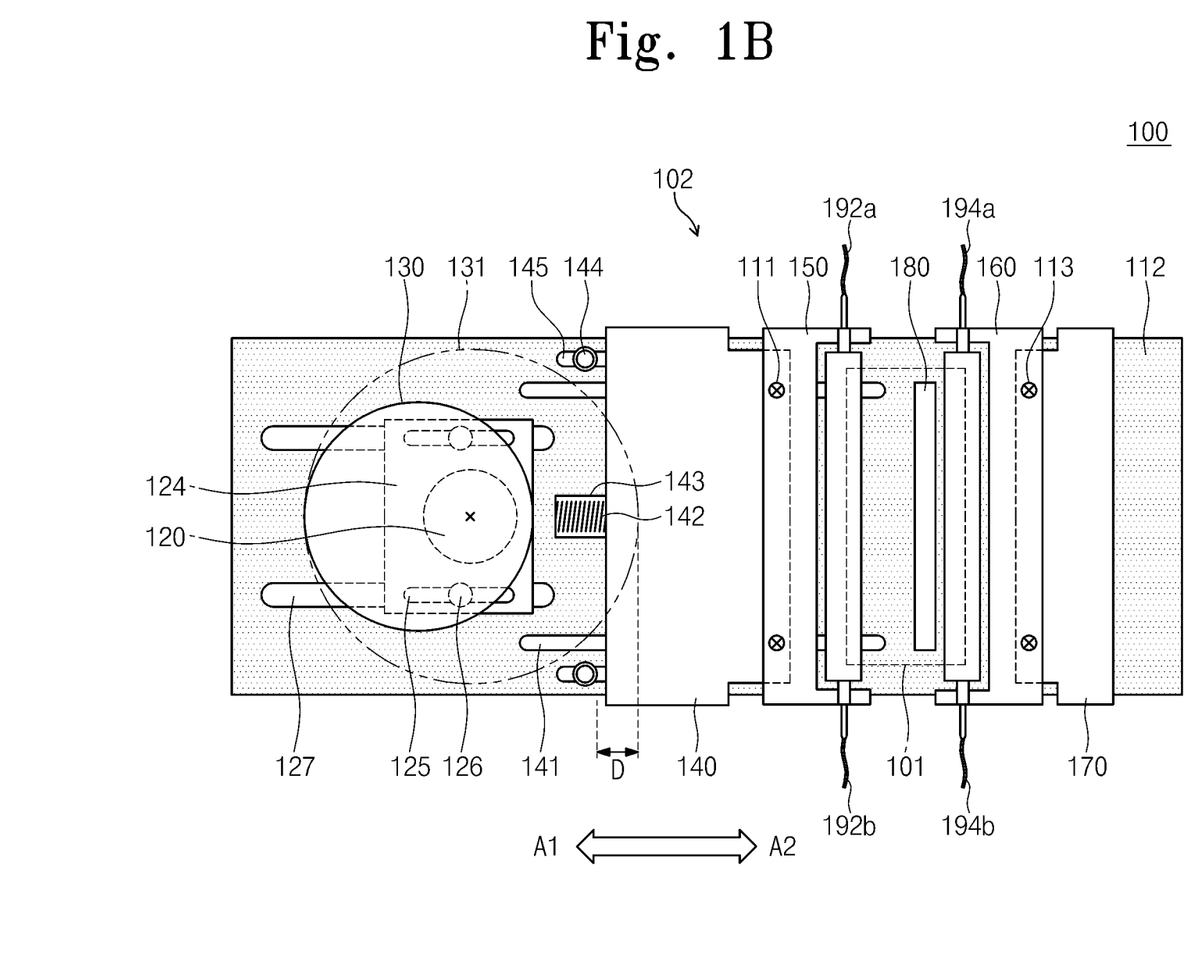
FIG. 1B is a plan view illustrating a bending test apparatus for a flexible device according to an embodiment of the present invention.

FIG. 1A is a sectional view illustrating a bending test apparatus for a flexible device according to an embodiment of the present invention. FIG. 1B is a plan view illustrating a bending test apparatus for a flexible device according to an embodiment of the present invention.

Referring to FIGS. 1A and 1B, the bending test apparatus 100 for a flexible device may include a test unit 102 in a housing 114 to test the reliability of the flexible device 101. According to an embodiment of the present invention, the test unit 102 may be designed to test reliability related to electrical and mechanical stresses of the flexible device 101. For example, according to the design of the bending test apparatus 100, a frame 112 may be installed in the housing 114 and the tester 102 may be provided to the frame 112.

The test unit 102 may include a motor generating a rotating motion, a cam 130 providing an eccentric rotation by receiving the rotating motion, a carrier 140 providing a linear reciprocating motion through the eccentric rotation of the cam 130, a first electrode part 150 connected to the carrier 140 and making a linear reciprocating motion possible, a second electrode part 160 loading the flexible device 101 also loaded into the first electrode part 150, and a fixing unit 170 fixing the second electrode part 160 at a predetermined position. According to this embodiment of the present invention, the first and second electrode parts 150 and 160 may be horizontally disposed. Furthermore, the first and second electrode parts 150 and 160 are designed to be rotatable during a bending test of the flexible device 101, such that uniform mechanical stress may be applied to the flexible device 101. The cam 130 may convert the rotating motion of the motor 120 into the linear reciprocating motion of the carrier 140.

The first and second electrode parts 150 and 160 are electrically connected to an electric device 190, and thus may apply an electrical signal to the flexible device 101. The electric device 190 may be a probe having a 4 terminal connection structure. For example, the first electrode part 150 may be electrically connected the electric device 190 through a first electrical wiring 192a and a second electrical wiring 192b for providing a delivery path of an electrical signal and the second electrode part 160 may be electrically connected to the electric device 190 through a third electrical wiring 194a and a fourth electrical wiring 194b for providing a delivery path of an electrical signal.

The first and second electrode parts 150 and 160 may be configured to apply mechanical stress to the flexible device 101. For example, at least one of the first and second electrode parts 150 and 160 may be designed to be movable to bend the flexible device 101. According to this embodiment of the present invention, the second electrode part 160 is fixed and the first electrode part 150 may linearly reciprocate to change an interval between the first and second electrode parts 150 and 160. For example, the first electrode part 150 may be fixed at the carrier 140 that linearly reciprocates in the left direction A1 and the right direction A2 such that it may linearly reciprocate depending on the linear reciprocating motion of the carrier 140. On the contrary, the second electrode part 160 may be fixed by a fixing unit fixed and installed at the frame 112. The first electrode part 150 may be combined with the carrier using a screw 111 and the second electrode part 160 may be combined with the frame 112 using a screw 115.

The linear movement to the right direction A2 of the carrier 140 may be accomplished by the motor 120 and the cam 130 connected to a shaft of the motor 120. The carrier 140 may linearly move along a first movement groove 141. The first movement groove 141 may be disposed on or in the frame 112. The cam 130 may have a disk structure and may be combined with the motor 120 to have an eccentric rotation. For example, the cam 130 may be combined with the motor 120 to allow its rotation axis to be offset with respect to the rotation axis I-I' of the motor 120. When the shaft 122 rotates by an operation of the motor 120 based on the rotation axis I-I', the cam 130 generates an eccentric rotation. Due to this eccentric rotation of the shaft 122, the carrier 140 may move to the right direction A2. Accordingly, the first electrode part 150 moves toward the second electrode part 160, such that the flexible device 101 may be bent. The flexible device 101 may be bent in an upper direction, a lower direction or both directions. According to this embodiment of the present invention, a supporter 180 may be included to bend the flexible device 101 in one of the upper and lower directions (for example, the upper direction B). The supporter 180 supports the flexible device 101 from the bottom thereof. As a result, when the flexible device 101 is bent, its initial direction may be in the upper direction. Accordingly, the flexible device 101 may be prevented from being bent in the gravitational direction.

A linear movement to the left direction A1 of the carrier 140 may be realized by a spring. One end of the spring 142 is fixed and the other end is connected to the carrier 140, such that the spring 142 may be designed to extend when the carrier 140 moves to the right direction A2. Accordingly, as the cam 130 becomes far from the carrier 140 through eccentric rotation, the carrier 140 linearly moves to the left direction A1 by a restoring force and thus may be positioned at the initial point. Accordingly, the first electrode part 150 becomes far from the second electrode part 160. When the carrier 140 deviates from the restoring point (i.e., the initial point), it can be stopped by a stopper 144. The left end of the spring 142 may be fixed at the frame 12 and its right end may be connected to the carrier 140. For example, as shown in FIG. 1B, a groove 143 may be prepared in the frame 112 and the spring 142 may be installed in the groove 143.

The motor 120 may be designed to allow its position to move to the left and right directions A1 and A2. For example, the motor 122 may be combined with a sliding plate 124 that is movable in the left direction A1 and the right direction A2. If the motor 120 moves to the right direction A2, the carrier 140 moves to the right direction A2 further. Thus, mechanical stress applied to the flexible device 120 may become great. According to this embodiment of the present invention, an amount of mechanical stress applied to the flexible device 101 may be adjusted by changing the position of the motor 120.

The bending test apparatus 100 of the present invention, as mentioned above, may be designed to adjust the amount of mechanical stress. For example, as shown in FIG. 1B, the motor 120 is combined with a fixing groove 125 using a fixing pin 126. The sliding plate 124 may be designed to freely move to the left direction A1 and the right direction A2 along a second sliding groove 127. Accordingly, the motor 120 may be movable in the left and right directions A1 and A2 along the second sliding groove 127. The fixing groove 125 may be prepared in or on the sliding plate 124.

The maximum moving distance D of the carrier 140 may be defined as the distance between the right end of the maximum eccentric rotation trajectory that the cam 130 draws and the stopper 144. If the motor 120 moves to the right direction A2 along the second sliding groove 127, since its trajectory 131 is moved to the right direction A2, the maximum moving distance D of the carrier 140 becomes large. Accordingly, an amount of mechanical stress applied to the flexile device 101 may become large. On the contrary, if the motor 120 moves to the right direction A1 along the second sliding groove 127, since the maximum moving distance D of the carrier 140 becomes small, the maximum moving distance D of the carrier 140 becomes small. Accordingly, an amount of mechanical stress applied to the flexile device 101 may become small.

The bending test apparatus 100 may be designed to allow the position of the stopper 144 to be movable to the left direction A1 and the right direction A2. For example, as shown in FIG. 1B, the stopper 144 may be designed to be movable in the left direction A1 and the right direction A2 along a third sliding groove 145. The third moving groove 145 may be prepared in or on the frame 112.

As mentioned above, since the motor 120 and/or the stopper 144 in the bending test apparatus 100 are/is movable to the left direction A1 and the right direction A2, an amount of mechanical stress applied to the flexible device 101 may be adjustable or the maximum stress value may be arbitrarily set.

Figure 1C:
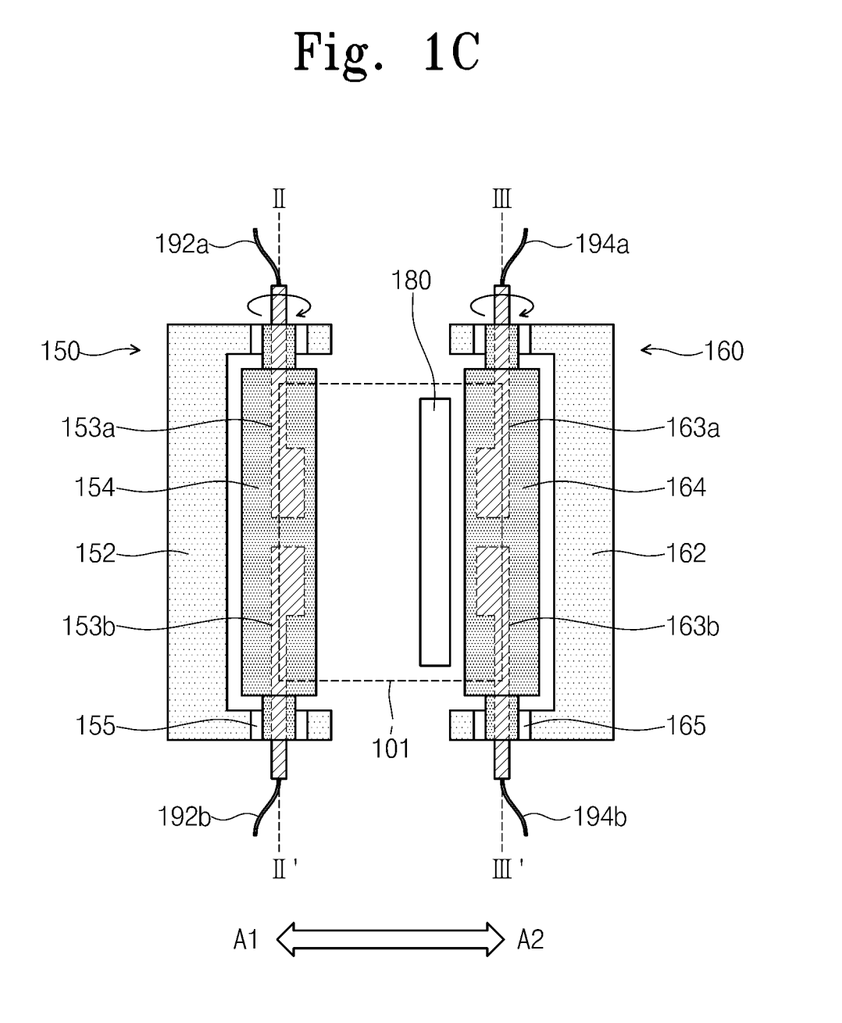
FIG. 1C is a plan view of an enlarged electrode part in a bending test apparatus of a flexible device according to an embodiment of the present invention.
Figure 1D:
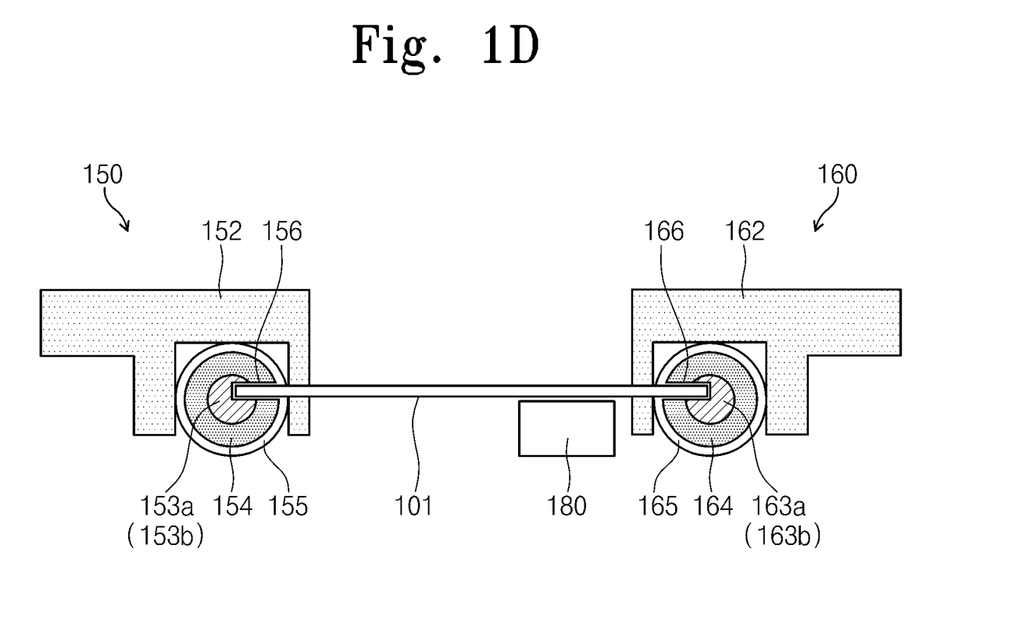
FIG. 1D is a sectional view of the enlarged electrode part.

FIG. 1C is a plan view of an enlarged electrode part in a bending test apparatus of a flexible device according to an embodiment of the present invention. FIG. 1D is a sectional view of the enlarged electrode part.

Referring to FIGS. 1C and 1D, the first electrode part 150 may include a first electrode body 152, a first roller 154 combined to the first electrode body 152 to be rotatable, and first and second metal electrodes 153a and 153b inserted in the first roller 154. The first roller 154 may have a cylindrical structure into which the flexible device 101 may be inserted. For example, a first groove 56 may be prepared in the roller 154 into which the flexible device 101 may be inserted. The left end of the flexible device 101 is inserted into the first groove 156 to ohmic-contact the first and second metal electrodes 153a and 153b, respectively. A first bearing 155 for reducing friction may be provided on the first electrode body 152 to allow the first roller 154 rotate smoothly. The first roller 154 may rotate based on the rotation axis II-II'. The rotation axis II-II' of the first roller 154 may be vertical to the horizontal directions A1 and A2. A first metal electrode 153a connected to a first electrical wiring 192a may be built at the top of the first roller 154, and a second metal electrode 153b connected to a second electrical wiring 192b may be built at the bottom. The first and second metal electrodes 153a and 153b may be formed of Al or Cu, for example.

The second electrode part 160 may be symmetric to the first electrode part 150. For example, the second electrode part 160 may include a second electrode body 162, a cylindrical second roller 164 combined to the second electrode body 162 to be rotatable based on the rotation axis III-III', and third and fourth metal electrodes 163a and 163b inserted in the second roller 164. The rotation axis III-III' of the second roller 164 may be horizontal to the rotation axis II-II' of the first roller 154 and may be vertical to the horizontal directions A1 and A2. The second roller 164 may have a structure through which the flexible device 101 may be inserted. For example, a second groove 166 providing a space into which the flexible device 101 is inserted may be prepared in the second roller 164. The right end of the flexible device 101 may be inserted in the second groove 166 to ohmic-contact the third and fourth metal electrodes 163a and 163b the third metal electrode 163a connected to a third electrical wiring 194a may be built at the top of the second roller 164, and a fourth metal electrode 163b connected to a fourth electrical wiring 194b may be built at the bottom of the second roller 164. The third and forth metal electrodes 163a and 163b may be formed of Al or Cu, for example.

In another example, only one of the first and second metal electrodes 153a and 154b may be built in the first roller 154 and only one of the third and fourth metal electrodes 163a and 164b may be built in the second roller 164. In this case, the electric device 190 shown in FIG. 1A may be a probe having two terminals.

As mentioned above, the supporter 180, which can deter the flexible device 101 from being bent in the lower direction, i.e., the gravity direction, may be disposed between the first electrode part 150 and the second electrode part 160. The supporter 180 may have a height identical to or higher than the radius of the first roller 154 or the second roller 164.

Figure 2A:
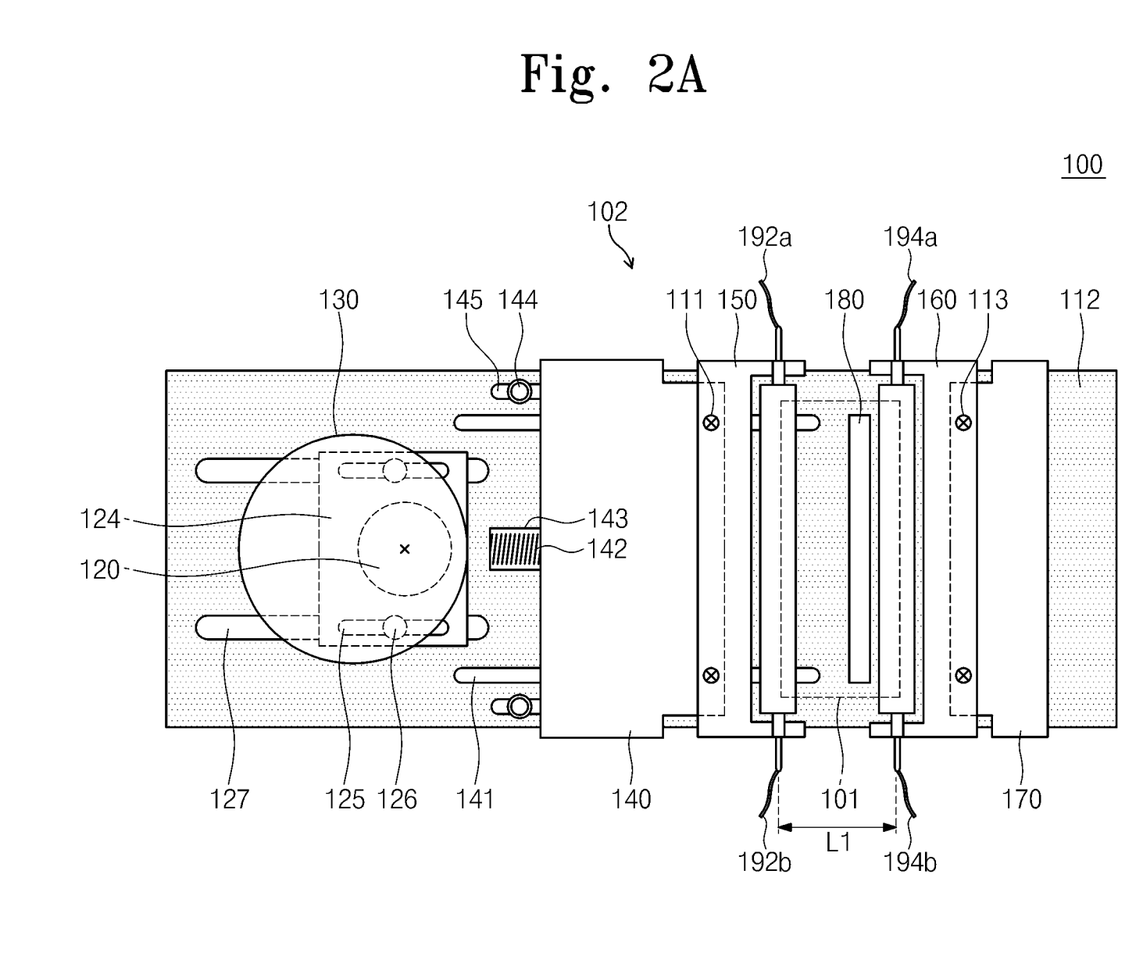
FIGS. 2A and 3A are plan views illustrating a bending test method of a flexible device according to an embodiment of the present invention.
Figure 2B:
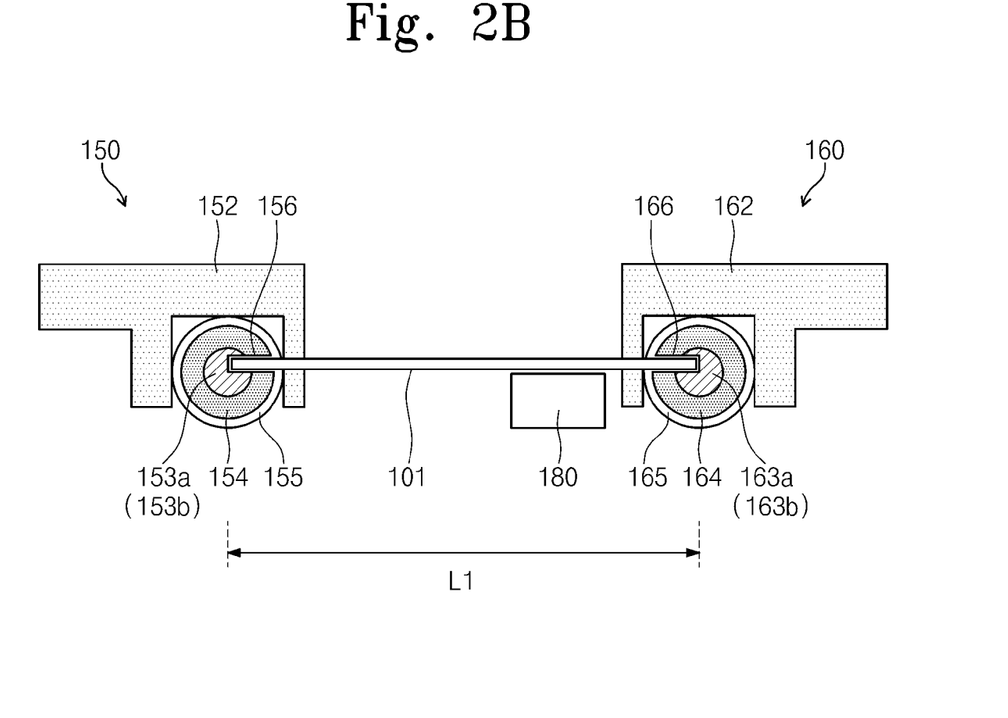
FIGS. 2B and 3B are sectional views of an enlarged electrode part.
Figure 3A:
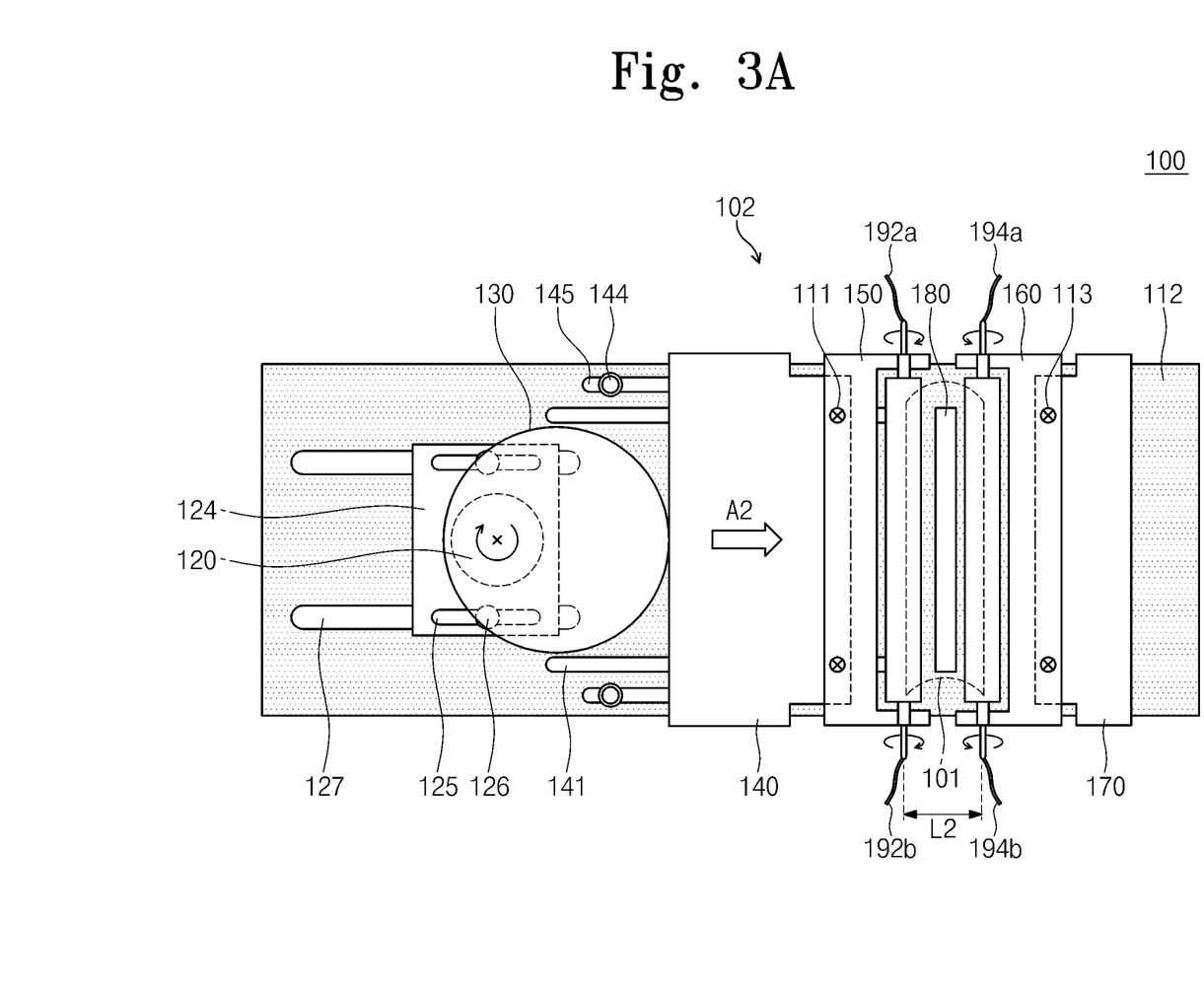
Figure 3B:
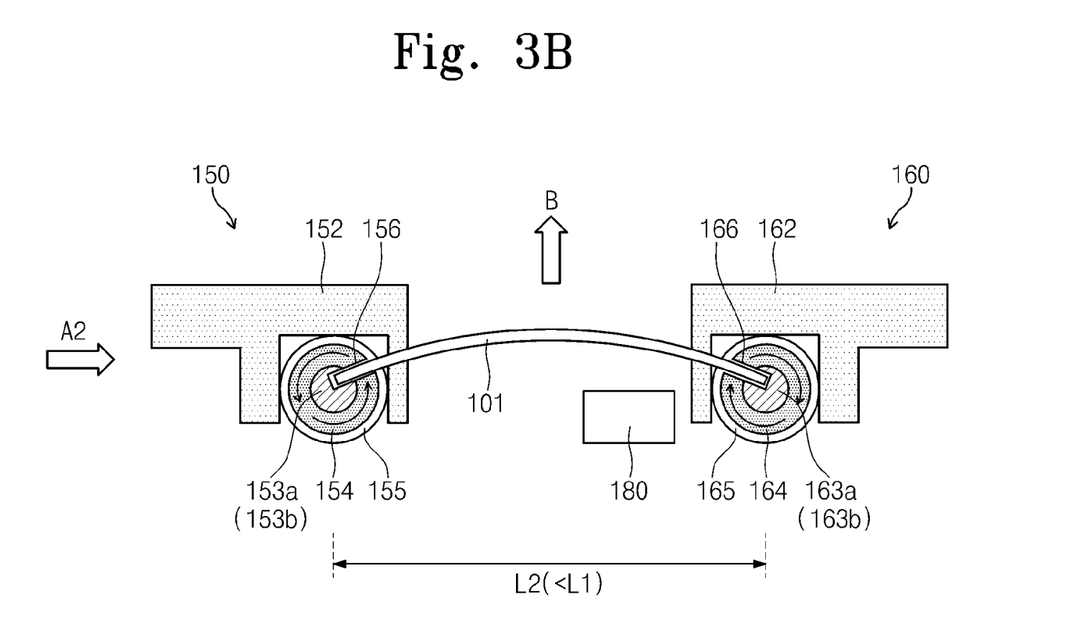

FIGS. 2A and 3A are plan views illustrating a bending test method of a flexible device according to an embodiment of the present invention. FIGS. 2B and 3B are sectional views of an enlarged electrode part.

Referring to FIGS. 2A and 2B, the flexible device 101 may be loaded between the first electrode part 150 and the second electrode part 160. The flexible device 101 may be supported horizontally. The first and second electrode parts 150 and 160 may be spaced by the first distance L1. The flexible device 101 may include an e-paper where a thin film is formed on a plastic substrate such as a polyimide substrate or a liquid crystal or organic light emitting display device but the present invention is not limited thereto. In this operation, mechanical stress is not applied to the flexible device 101 yet and thus the flexible device 101 may be in a flat state. Selectively, in this operation, after electrical stresses or electrical signals are applied to the first electrode part 150 through the first and second electrical wirings 192a and 192b and then are applied to the second electrode part 160 through the third and fourth electrical wirings 194a and 194b, the flexible device 101 may be electrically tested.

Referring to FIGS. 3A and 3B, a bending test may be performed by applying mechanical stress to the flexible device 101. For example, if the motor 120 generates rotator power, the cam 130 receives the rotator power and generates eccentric rotation. The eccentrically-rotating cam 130 linearly moves the carrier 140 to the right direction A2 and thus the first electrode part 150 may move toward the second electrode part 160. Accordingly, the first distance between the first electrode part 150 and the second electrode part 160 narrows into the second distance L2, such that the flexible device 101 become bent. The flexible device 101 to which mechanical stress is applied is not bent toward the bottom due to the supporter 180 but is bent toward the top B. Resistance or output current may be measured by applying electrical stresses or signals to the bent flexible device 101.

According to this embodiment of the present invention, since the first roller 154 and the second roller 164 are rotatable, the flexible device 1000 may be bent in the uniform radius of curvature during a bending test. For example, as shown in FIG. 3B, when the first electrode part 150 moves toward the second electrode part 160, mechanical stress may be applied to the flexible device 101. At this point, since the first roller 154 rotates in a clockwise direction and the second roller 164 rotates in a counterclockwise direction, uniform mechanical stress may be applied to the flexible device 101. If an inflection point occurs because the flexible device 101 is bent in the irregular radius of curvature, directions of mechanical stress around the inflection point may change. In this case, since mechanical stress applied to the flexible device 101 is not uniform, reliability of the bending test cannot be achieved. However, according to an embodiment of the present invention, since the flexible device 101 can be bent in the uniform radius of curvature, mechanical stress also can be uniformly maintained. Accordingly, reliability of a bending test about the flexible device 101 can be achieved.

According to this embodiment of the present invention, since mechanical stress can be horizontally applied to the flexible device 101, gravity effect can be excluded. If mechanical stress applied to the flexible device 101 is in the gravity direction, gravity can be added further. Due to the gravity added to the flexible device 101, mechanical stress is not uniform, such that it may be difficult to achieve reliability of the bending test. However, since mechanical stress in a horizontal direction, for example, the right direction A2, is applied to the flexible device 101, uneven mechanical stress due to the gravity does not occur.

Figure 4A:
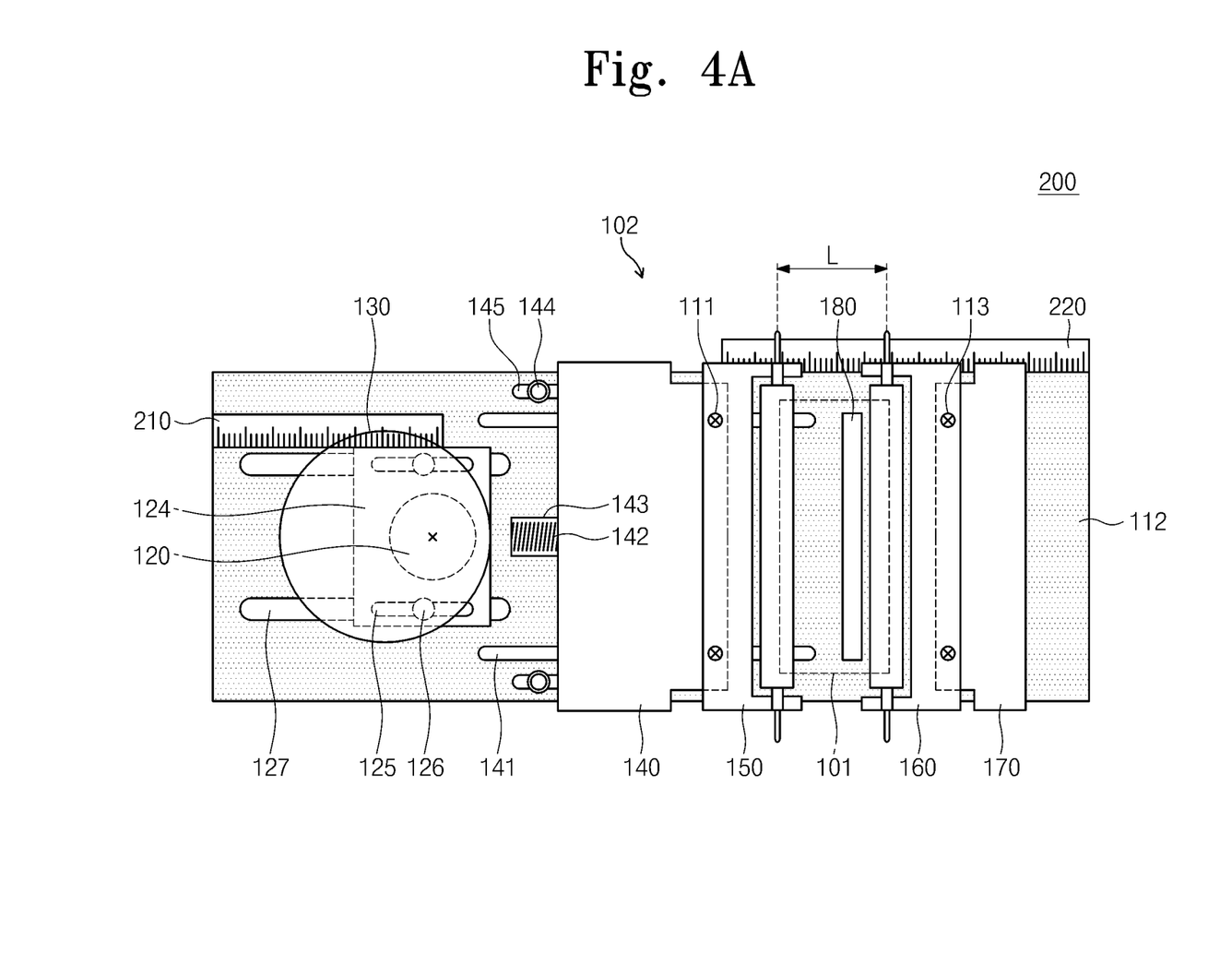
FIGS. 4A and 4B are plan views illustrating a bending test apparatus of a flexible device according to a modified embodiment of the present invention.
Figure 4B:
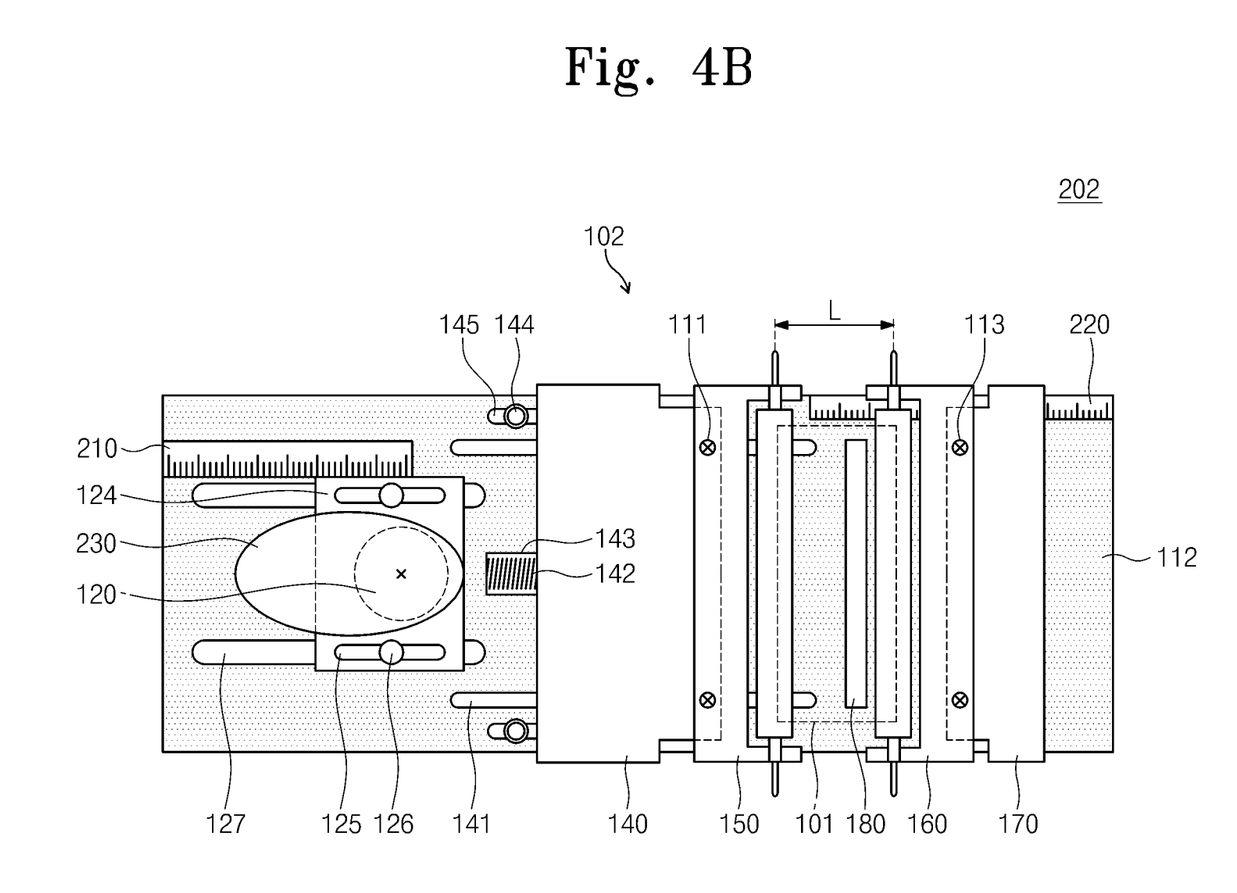

FIGS. 4A and 4B are plan views illustrating a bending test apparatus of a flexible device according to a modified embodiment of the present invention. Since this modified embodiment is similar or identical to the above embodiment, only differences therebetween will be described in detail and their overlapping description will be omitted.

Referring to FIG. 4A, a bending test apparatus 200 may include at least one of a first ruler 210 estimating a position of a motor 120 and a second ruler 220 estimating a distance L between first and second electrode parts 150 and 160. For example, the first ruler 210 may be disposed on the top of the frame 112 or may be drawn on the top of the frame 112. The first ruler 210 may be disposed adjacent to the side of a sliding plate 124. The second ruler 220 may be disposed at one side of the frame 112. The second ruler 220 may be disposed adjacent to the sides of the first and second electrode parts 150 and 160.

Referring to FIG. 4B, the bending test apparatus 202 may include a first ruler 210, a second ruler 220, and an oval cam 230. The cam 230 is not limited to the oval shape, and thus may have an arbitrary shape. The second ruler 220 may be installed on the top of the frame 112 below the first and second electrode parts 150 and 160 and or may be drawn on the top of the frame 112.

According to the present invention, an electrode part loading a flexible device is installed horizontally and mechanical stress is applied in a horizontal direction. Thus, compare to applying mechanical stress in a vertical direction, more uniform mechanical stress can be applied. Moreover, since the electrode part is designed to be rotatable, more uniform mechanical stress can be applied. As a result, a flexible device can be bent in the uniform radius of curvature. Accordingly, inflection points do not occurs in the flexible device during a bending test, such that test reliability can be achieved.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A bending test apparatus of a flexible device, the apparatus comprising:
   first and second electrode parts disposed in a horizontal direction and loading a flexible device horizontally,
   wherein the flexible device has a first end and a second end opposite to the first end in the horizontal direction, and
   wherein the first electrode part is movable in the horizontal direction and the second electrode part is fixed so that the first electrode part horizontally moves toward the second electrode part to apply mechanical stress of the horizontal direction to the flexible device, and a distance between the first and second ends of the flexible device is reduced by the movement of the first electrode part toward the second electrode part.

2. The apparatus of claim 1, wherein at least one of the first and second electrode parts is rotatable based on a rotation axis vertical to the horizontal direction.

3. The apparatus of claim 1, further comprising a supporter disposed between the first and second electrode parts and preventing the flexible device to which the mechanical stress of the horizontal direction is applied from being bent in a gravity direction.

4. The apparatus of claim 1, further comprising an electric device providing electrical signals to the first and second electrode parts to apply electrical stress to the flexible device.

5. A bending test apparatus of a flexible device, the apparatus comprising:
   a motor generating a rotating power;
   a cam connected to the motor and eccentrically rotating by receiving the rotating power;
   a carrier linearly moving in a horizontal direction by the eccentric rotation of the cam;
   a rotatable first electrode part fixed at the carrier and moving in the horizontal direction depending on the linear movement of the carrier; and
   a rotatable second electrode part fixed and spaced apart from the first electrode part in the horizontal direction;
   wherein:
   the first and second electrode parts load horizontally a flexible device;

the flexible device has a first end and a second end opposite to the first end in the horizontal direction; and the first electrode part moves toward the second electrode part and a distance between the first and second ends of the flexible device is reduced by the movement of the first electrode part toward the second electrode part.

6. The apparatus of claim 5, wherein the motor is movable in the horizontal direction.

7. The apparatus of claim 5, wherein the cam and the carrier are disposed in the horizontal direction.

8. The apparatus of claim 5, wherein:
the horizontal direction has opposite first and second horizontal directions;
the first electrode part moves toward the second electrode part depending on movement to the second horizontal direction of the carrier; and
a distance between the first and second electrode parts is reduced by the movement of the first electrode part to apply mechanical stress of the horizontal direction to the flexible device.

9. The apparatus of claim 8, further comprising a spring combined to the carrier and restoring the carrier to the first horizontal direction.

10. The apparatus of claim 8, further comprising a stopper disposed between the carrier and the cam and preventing excessive movement of the carrier to the first horizontal direction that exceeds a restoring position of the carrier.

11. The apparatus of claim 10, wherein the stopper is movable in the horizontal direction.

12. The apparatus of claim 5, wherein at least one of the first and second electrode parts comprises:
a roller including a groove into which the flexible device is inserted;
at least one electrode disposed in the roller and electrically contacting the flexible device inserted into the groove; and
an electrode body installed and allowing the roller to be rotatable,
wherein the roller rotates when the flexible device is bent to apply uniform mechanical stress to the flexible device.

13. The apparatus of claim 12, further comprising a probe of a terminal connection structure applying electrical stress to the flexible device by applying an electrical signal to the at least one electrode.

14. The apparatus of claim 12, further comprising a supporter disposed between the first and second electrode parts, having a height identical to or higher than a radius of the roller and preventing the flexible device from being bent in a gravity direction.

15. The apparatus of claim 5, further comprising at least one of a first ruler estimating a position of the motor and a second ruler estimating a distance between the first and second electrode parts.

16. The apparatus of claim 5, wherein a rotation axis of the cam is offset with respect to a rotation axis of the motor.

17. The apparatus of claim 5, further comprising a frame providing a place into which the first and second electrode parts and the carrier are installed, the frame including a first moving groove that guides the carrier in the horizontal direction.

18. The apparatus of claim 17, wherein the frame further comprises a second moving groove changing a position of the motor and a third moving groove changing a position of the stopper.

19. A bending test apparatus of a flexible device, the apparatus comprising:
a device converting a rotating motion into a linear reciprocating motion;
a first electrode part combined with the device and providing a linear reciprocating motion together in company with the device; and
a second electrode part disposed being horizontally spaced apart from the first electrode part and horizontally loading the flexible device between the first electrode part and the second electrode part,
wherein:
the first and second electrode parts load horizontally a flexible device;
the flexible device has a first end and a second end opposite to the first end in the horizontal direction; and
the first electrode part linearly moves toward the second electrode part to bend the flexible device vertically and a distance between the first and second ends of the flexible device is reduced by the linear movement of the first electrode part toward the second electrode part.

20. The apparatus of claim 19, wherein the device comprises:
a motor generating the rotating motion;
a carrier combined with the first electrode part and providing the linear reciprocating motion by receiving the rotating motion; and
a cam combined with the motor, eccentrically rotating by the rotating motion, and linearly moving the carrier toward the second electrode part,
wherein the cam converts the rotating motion of the motor into the linter reciprocating motion of the carrier.

* * * * *